United States Patent
Calandruccio et al.

(10) Patent No.: US 8,617,251 B2
(45) Date of Patent: Dec. 31, 2013

(54) TRAPEZIUM IMPLANT FOR THUMB AND METHOD

(75) Inventors: James H. Calandruccio, Memphis, TN (US); Mark T. Jobe, Memphis, TN (US); Chad J. Patterson, Bartlett, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 0 days.

(21) Appl. No.: 13/423,405

(22) Filed: Mar. 19, 2012

(65) Prior Publication Data

US 2012/0179267 A1   Jul. 12, 2012

Related U.S. Application Data

(62) Division of application No. 10/842,030, filed on May 7, 2004, now abandoned.

(51) Int. Cl.
*A61F 2/42* (2006.01)

(52) U.S. Cl.
USPC .................. 623/21.15; 623/21.11; 623/21.19

(58) Field of Classification Search
USPC ........................................ 623/21.11–21.19
See application file for complete search history.

(56) References Cited

U.S. PATENT DOCUMENTS 3,924,276 A * 12/1975 Eaton .................. 623/21.15
4,355,427 A * 10/1982 Schneider ............ 623/19.14

* cited by examiner

*Primary Examiner* — Thomas J Sweet
*Assistant Examiner* — Christopher D Prone
(74) *Attorney, Agent, or Firm* — Duane Morris LLP

(57) ABSTRACT

An implant for the trapezium of the thumb carpometacarpal (CMC) joint comprising an integral elastomeric member configured to include a body portion having a tapered neck, having extending from one end thereof an elongated, longitudinally extending tapered portion adapted to be embedded into a reamed out-channel in the thumb metacarpal bone. After implantation, in the preferred embodiment of the method according to the invention, a segment of a nearby tendon, for example, the APL or FCR tendons, may be wrapped around the tapered neck of the implant to secure it in position, thereby forming a reinforced structure to inhibit dislocation of the prosthesis. However, in other methods, various other securing elements, including, but not limited to acellular matrices, may be used to retain the implant in position.

14 Claims, 3 Drawing Sheets

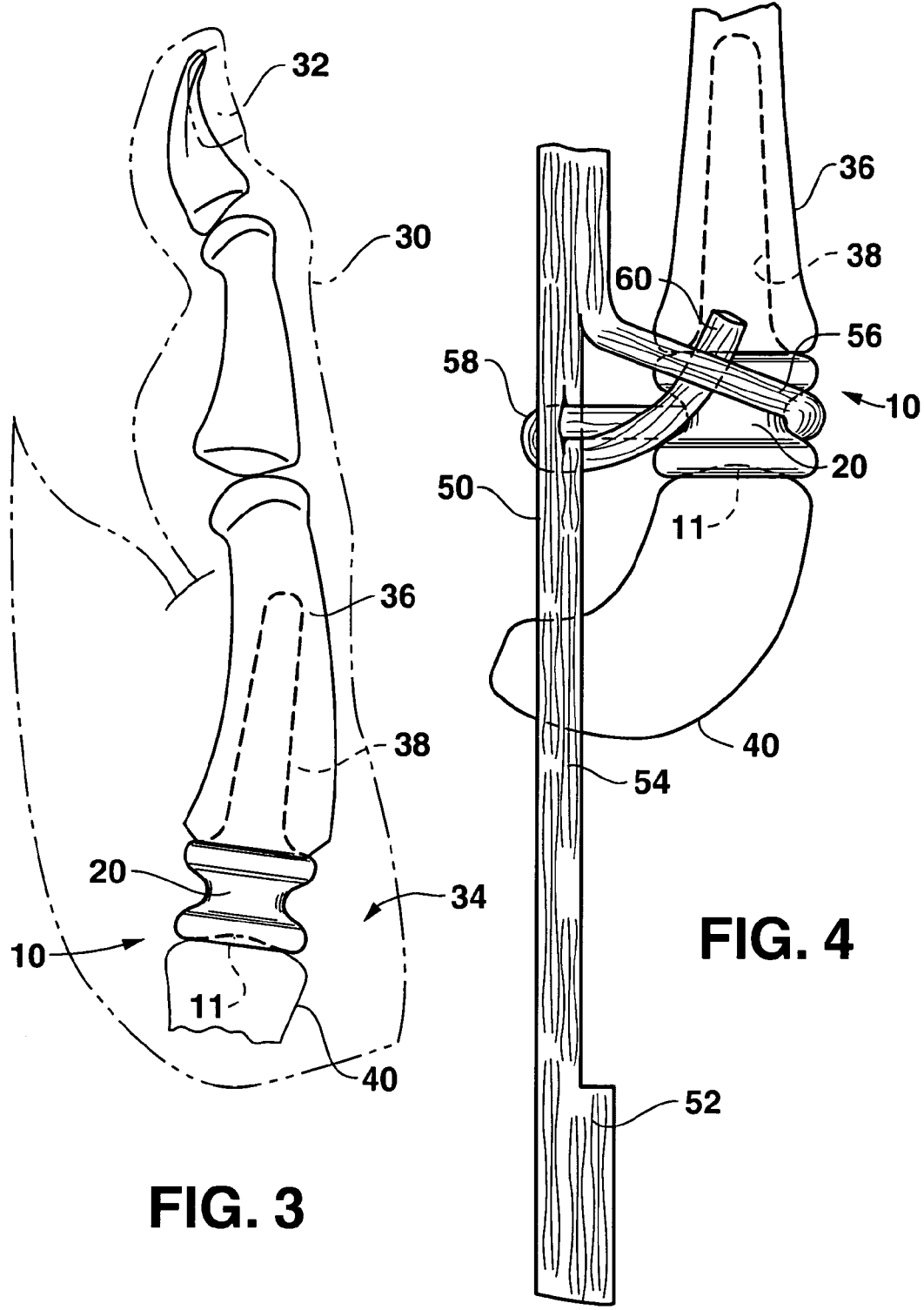

TRAPEZIUM IMPLANT FOR THUMB AND METHOD

CROSS-REFERENCE TO RELATED APPLICATIONS

This application is a divisional application of U.S. patent application Ser. No. 10/842,030, filed on May 7, 2004, the entirety of which is herein incorporated by reference.

BACKGROUND OF THE INVENTION

Freedom from pain is essential for normal thumb function. Although the carpometacarpal (CMC) joint of the thumb is described as a saddle joint, it is actually formed by apposed saddles, one astride the other, each one's longitudinal axis perpendicular to the other. Such a relationship creates a joint where two primary planes of motion, flexion-extension and adduction-abduction, are perpendicular to one another. With rotary movement such as opposition and circumduction, the surfaces are twisted into a less congruous relationship, causing tightening of the joint capsule and thereby increasing joint stability, provided all ligaments are competent.

Idiopathic hypermobility of the thumb basal joint is not uncommon, particularly in women, and would seem to be a major factor in producing the arthrosis which so frequently afflicts the CMC joint. Trauma, acute or recurrent, causing partial tears or stretching of the ligaments, likewise will produce varying degrees of hypermobility. Undetected articular damage may also accompany such trauma, thereby compounding the pathological process. When painful hypermobility is present, restoration of ligament stability will not only relieve the pain and stabilize the joint, but, when done prior to the onset of articular damage, may prevent or at least retard subsequent joint degeneration. A ligament reconstruction procedure for painful, unstable thumb carpometacarpal (CMC) joint is presented in an article entitled "Ligament Reconstruction for the Painful Carpometacarpal (CMC) Joint," by Eaton, and Littler, which appears in the Journal of Bone and Joint Surgery, Vol. 55-A, No. 8, pp. 1655-1666, December, 1973.

For more advanced arthrosis, ligament reconstruction is not sufficient. Advanced arthrosis is generally recognized by the obvious dorsal subluxation of the metacarpal base. As the base of the thumb metacarpal subluxates dorsally, there is a reciprocal flexion-abduction of the metacarpal shaft, and frequently flexion-adduction contracture of the entire thumb ray. Carried to the extreme deformity, the metacarpophalangeal joint compensates for the metacarpal flexion-adduction position by hyperextending and the joint may become fixed in this hyperextended position. These sequential compensation deformities must be recognized and corrected at the same time as reconstruction of the basal joint is carried out.

Heretofore, deformities of the carpometacarpal (CMC) joint have been undertaken utilizing a trapezium prosthesis, and implanting the prosthesis following removal of the diseased trapezium bone. One known prosthesis comprises an integral elastomeric member, preferably of a flexible silicone material, having a cylindrical base portion from one end of which extends a triangular cross-sectioned tapered projection adapted to be imbedded into the reamed-out channel in the thumb metacarpal bone. In view of the very slippery, low coefficient surface of the material of the prosthesis, and the fact that the elastomeric material of the prosthesis is difficult to handle and will not hold a stitch, when implanted, the prior art prosthesis has a tendency to slip out of place in that the opposite end of the cylindrical portion of the prosthesis merely rests against the adjacent navicular. Furthermore, when implanted, the amount of force applied by the patient, in a pinching direction of the hand, must be limited in order to prevent inadvertent popping out of the prior art prosthesis. Still further, in order to insure as close a fit as possible, in order to minimize slipping out of position of the prosthesis, several different sizes of prosthesis must be manufactured, and by trial and error implanted into the patient's hand.

Another form of known prosthesis or trapezium prosthesis is of the general shape of the prior art device described above with the addition of several elastomeric tails or extending elements which are looped around a structure of the palmer aspect of the hand in an attempt to keep the prosthesis from dislocating dorsally.

As is readily apparent, considering the type of material which must be employed for an implantable prosthesis, the tails or extending elements are extremely fragile, and tend to wear and break thereby losing the fixation sought to be obtained. In addition, it is difficult to firmly secure the elastomeric tails to the hand structure, thereby resulting in the patient having to limit the use of his hand with reference to the application of hand grip forces.

Accordingly, there is room for improvement within the art.

OBJECTS OF THE INVENTION

It is an object of the invention to provide a trapezium implant of increased strength and longevity.

It is an object of the invention to provide a trapezium implant that is less likely to become dislodged from its proper positioning.

It is an object of the invention to provide a trapezium implant that is easy to implant and firmly position.

These and other objects of the invention are achieved by an implant for the trapezium of the thumb carpometacarpal joint comprising an integral, elastomeric member including a body portion having: an elongated, longitudinally extending tapered portion extending from one end of the body portion; and a tapered neck.

These and other objects of the invention are achieved by a method of reconstructing the carpometacarpal (CMC) joint of a thumb, including the steps of: a) implanting an implant having an elongated tapered portion and a tapered neck into the joint; b) stripping away a portion of tendon, leaving the distal attachment intact adjacent the implant; c) wrapping the split tendon around the tapered neck of the implant to a point intersecting the remaining tendon at the palm side of the hand, and suturing the split tendon to the remaining tendon.

These and other objects of the invention are achieved by a method of reconstructing the carpometacarpal (CMC) joint of a thumb, including the steps of: a) implanting an implant having an elongated tapered portion and a tapered neck into the joint; b) providing a securing element; c) attaching the securing element to a tendon; d) wrapping the securing element around the tapered neck of the implant to a point intersecting the tendon at the palm side of the hand, and attaching the securing element to the tendon.

BRIEF DESCRIPTION OF THE DRAWINGS

FIG. 3 is a top view of a thumb and the surgically implanted exemplary embodiment of the trapezium prosthesis according to the subject invention; and FIG. 4 schematically illustrates the completed surgically implanted exemplary embodiment of the trapezium prosthesis as firmly fixed in place in an exemplary method by the use of a portion of the patient's natural tendon.

DETAILED DESCRIPTION OF THE INVENTION

With reference to the figures, an exemplary embodiment of a trapezium prosthesis/implant for the thumb that meets and achieves all the above-mentioned objects of the invention will now be described.

Figure 1:
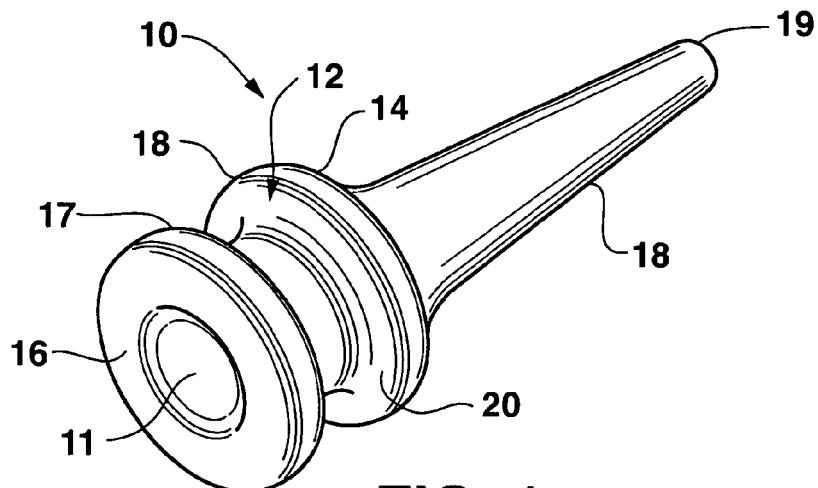
FIG. 1 is a perspective view of an exemplary embodiment of a trapezium prosthesis according to the subject invention.
Figure 2:
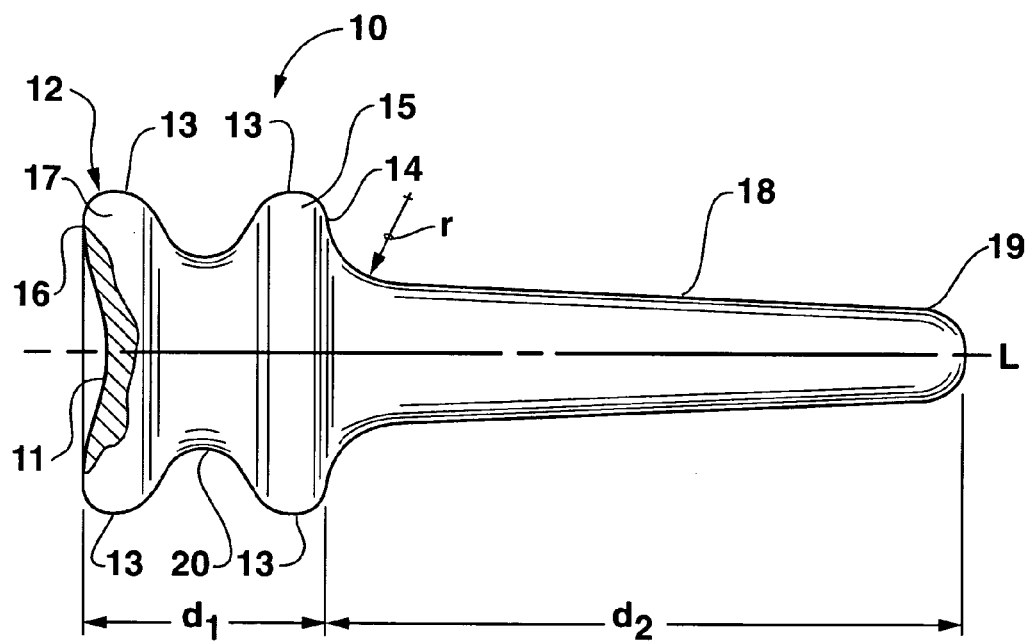
FIG. 2 is a side view of of an exemplary embodiment of a trapezium prosthesis according to the subject invention.

Referring to FIGS. 1 and 2, the exemplary embodiment of the trapezium implant according to the invention is generally designated by the numeral 10 and comprises an integral elastomeric member, preferably a silastic material such as silicone rubber, and which is inherently flexible and physiologically inert. The implant 10 includes a body portion 12 having tapered conical portions 15 and 17 separated by a tapered neck 20. Tapered portions 15 and 17 have end faces 14 and 16, respectively. Integrally formed and projecting from the end face 14 is an elongated, longitudinally extended tapered portion 18 which extends along the longitudinal axis L of implant 10. Tapered portion 18 will have a length $d_2$ that is typically equal to 3 (three) times the length $d_1$ of body portion 12 so as to assure the overall integrity of the reconstructed joint. Tapered portion 18 should preferably have a substantially constantly decreasing taper (at least in the area of end 19), unlike the more variable taper shown in the implant depicted in U.S. Pat. No. 3,924,276, whose contents are incorporated by reference herein in their entirety. The end 19 of the tapered portion 18 is blunted, preferably with a generally hemispherical tip only at its end, unlike the more pointed configuration shown in the '276 patent. The tapered portion 18 has a preferably generally annular (i.e., circular) cross-section to reduce residual stresses in implant 10. However, polygonal cross-sections, such as triangular cross-sections described above, may be used. Additionally, the proximal end of tapered portion 18 should merge into end face 14 of tapered portion 15 via a sweeping curve, typically having a radius r of approximately 3/32 inches. A sweeping curve, rather than a sharp projection such as shown in the '276 patent or other prior art trapezium implants, assures the structural integrity of the overall implant.

The opposite end face 16 of body portion 12 has a slightly concave depression 11 in order to more effectively cooperate with the navicular or scaphoid bone 40 (see FIGS. 3 and 4), as will be more particularly described hereinafter.

As previously mentioned, extending transverse to the longitudinal axis L of the implant 10, and more particularly radially through the body portion 12 is a tapered neck 20. Tapered neck 20 will preferably have a circular cross-section. The diameter of the tapered neck 20 is suitably dimensioned relative to the size of the body portion 12 and the material from which it is made to prevent breaking of the implant 10, and yet small enough to fully accommodate the portion of the tendon which is to be wrapped there around, as will be described below. Rims 13 of tapered portions 15, 17 should preferably be rounded, rather than squared to reduce residual stresses in implant 10 and increase its overall strength and longevity.

FIGS. 3 and 4 illustrate steps in the method of applicant's invention. As shown in FIG. 3, in the subject process of reconstructing the thumb carpometacarpal (CMC) joint 34 following the surgical removal of the diseased trapezium, the surgeon then performs the step of hollowing out the lining of the marrow cavity of the metacarpal bone 36 utilizing conventional techniques and conventional apparatus such as an electric reaming device in order to define any elongated cavity 38 in the metacarpal bone 36. The implant 10, and more particularly the elongated extended portion 18, is inserted into the cavity 38. The base or end face 16 of the implant 10 should fit in good contact circumferentially with the cortex or outer portion of the thumb metacarpal 36 so that it has even pressure around the entire contact surface. Likewise the opposite end face 16, with its slightly concave depression 11, should fit in good firm contact with the navicular or scaphoid 40. In some cases, it may also be desirable to sculpt the lower 5 mm of the trapezoid (not shown) to permit the lower portion of the implant 10 to sit atop the scaphoid 40 while not interfering with the scaphotrapezoid joint (not shown). Reference should be made to U.S. Pat. No. 5,913,818, commonly assigned with this patent application and incorporated by reference herein, for a depiction of the relationship of the trapezoid to the scaphoid.

The next step in the preferred method is to obtain a strip of adjacent tendon, for which is suggested the use of the abductor pollicis longus (APL) tendon or the flexor carpi radialis (FCR) tendon. Through conventional technique, two incisions are made above the wrist, and the main tendon body 50 is partially cut across its width as at 52, and stripped along the longitudinal line 54 to obtain a strip 56 of about 6 centimeters in length. However, the doctor has great flexibility in this regard. This segment 56 is tunneled under the skin to emerge at the wrist in the vicinity of the metacarpal joint, after which the free end of the tendon strip 56 is directed around the tapered neck 20 of the implant 10 (see FIG. 4) and then penetrated through the residual capsule attached to the metacarpal 36 at a point which is perpendicular to the plane of the thumb nail 32, and then the tendon strip 56 is passed to the remaining main tendon body, as at point 58, at the palm side of the new reconstructed joint. The strip 56 is fixed, such as by means of two stitches, to the main tendon body 50 on the dorsal side of the hand, at the point where it wraps around the tapered neck 20 the implant 10 on the dorsal of the wrist, and then likewise the implant 10 is pulled into place by pulling on the ligament, thereby seating it into its socket, and then a second suture is placed between this new ligament and the main tendon body 50. The free tail 60 usually represents about 4 centimeters, and this free tail is then interwoven across and around the implant 10 to form a new capsule for the metacarpal joint. The use of a tendon as a building material to weave a new capsule provides an extremely strong and durable construction, since it is thicker than the natural capsule, and of course, since it is the patient's own tissue it cannot and will not be rejected. It will adhere to any normal tissue, and it will not adhere to the elastomeric material of the implant 10. Of course, the tendon does not have to adhere to the implant 10 since it passes around the tapered neck 20 of the implant 10 and therefore firmly secured to the implant 10.

In some patients, where there is sufficient quality capsular tissue, suture (not shown) may be passed around the tapered neck 20 and sewn to the capsule to provide implant 10 stabilization; tendon will not have to be used.

While the preferred method according to the invention is to use, for example, a portion of the patient's APL or FCR tendon to keep implant 10 in position, the method is not so limited. First, connective tissue may be harvested from any other suitable location on the patient as is well known in the art. Second, and less preferable, allograft may be used after the proper tissue matching and pathogen purification protocols are followed. Third, organically derived acellular matrices, which do not pose tissue matching due to their processing, may be used. Examples of such matrices, used in other applications can be found in, for example, US Pub. 2002/072806; U.S. Pat. No. 6,206,931. However, a preferred acellular matrix would comprise Graftjacket® acellular matrix, sold by Wright Medical Technology, Inc., of Arlington, Tenn., and manufactured according to U.S. Pat. Nos. 4,865,871; 5,024,830; and 5,336,616. This product consists of a selectively preserved extracellular protein matrix that is devoid of certain viable cells which normally express major histocompatibility complex antigenic determinants and other antigens which would be recognized as foreign by the recipient. This extracellular protein matrix is made up of collagen and other proteins and provides a structural template which may be repopulated with new viable cells that would not be rejected by the host. With this material complications following implantation (including but not limited to immunorejection, contracture, calcification, occlusion, and infection) are significantly reduced relative to current implant procedures and materials. Finally, synthetic porous materials capable of connective tissue in-growth may be used. See e.g. U.S. Pat. No. 5,258,040.

Figure 5:
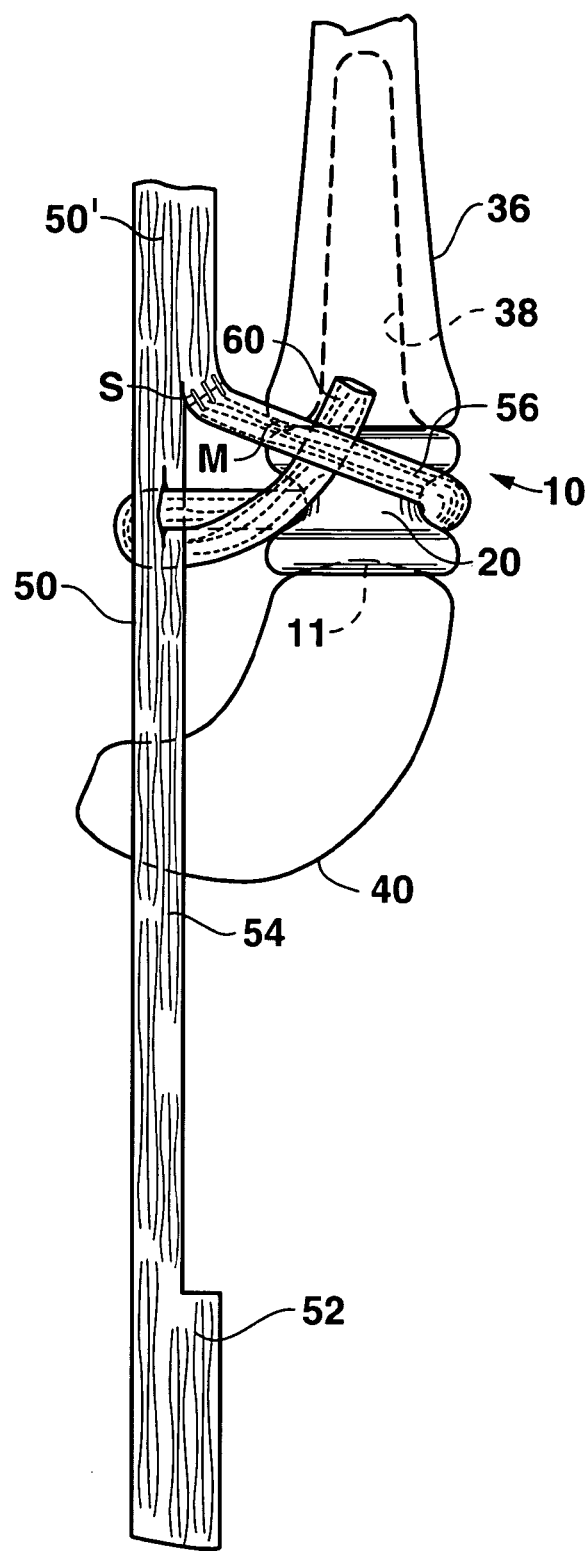
FIG. 5 schematically illustrates the completed surgically implanted second exemplary embodiment of the trapezium prosthesis as firmly fixed in place in an exemplary method by the use of a tendon substitute.

Any of these exemplary materials, comprising a tendon substitute, may be fixed to the existing tendon using any known method and then wrapped around implant 10 as described above. This is shown in FIG. 5. For example, material M is sutured to the distal portion 50' of tendon 50 using suture S. Then, material M is manipulated as tendon strip 56 described above was to secure implant M in position.

Therefore, using either the patient's natural tendon or a tendon substitute as a securing element in combination with implant 10, the resulting reconstructed metacarpal joint is significantly stronger, more durable, and easier to implant than prior art reconstructed joints using conventional prosthesis. For example, in U.S. Pat. No. 3,924,276, several shortcomings are inherent in the design. First, the radial aperture causes the overall implant to be weaker. Second, there is the additional step of properly aligning the aperture. Third, there is the overall difficulty in threading the tendon through the aperture. None of such steps or difficulties are present in the inventive design while all the benefits of the '276 patent are achieved if not exceeded, e.g., grip strength.

To those skilled in the art to which this invention relates, many changes in construction and widely different embodiments and applications of the subject process and device will suggest themselves without departing from the spirit and scope of the invention. The disclosures and descriptions herein are purely illustrative and are not intended to be in any sense limiting.

That which is claimed:

1. A method of reconstructing a carpometacarpal (CMC) joint of a thumb of a hand, comprising:
   a) implanting an implant having an elongated tapered portion and a tapered neck into the CMC joint such that the tapered neck that extends circumferentially about a body portion of the implant from which the elongated tapered portion extends is disposed adjacent to the bones of the CMC joint;
   b) stripping away a portion of a tendon to leave a distal attachment intact adjacent to the implant;
   c) wrapping the portion of the tendon around the tapered neck of the implant to a point intersecting a remaining tendon at a palm side of the hand in the absence of threading the tendon through an aperture such that the portion of the tendon is received within the tapered neck and at least partially encircles a longitudinal axis defined by the elongated tapered portion of the implant; and
   d) suturing the tendon to the remaining tendon.

2. The method of claim 1, wherein step b) includes stripping away a portion of a flexor carpi radialis (FCR) tendon.

3. The method of claim 1, wherein step b) includes stripping away a portion of an abductor pollicis longus (APL) tendon.

4. The method of claim 1, wherein the elongated tapered portion is inserted into a cavity formed in a metacarpal until an end face of an internal bulge of the implant circumferentially contacts a cortex of the metacarpal.

5. The method of claim 4, wherein the tapered neck is disposed between the internal bulge and an articulation bulge of the implant.

6. The method of claim 5, wherein the tapered neck has a cross-sectional area that is less than a cross-sectional area of the internal bulge and a cross-sectional area of the articulation bulge.

7. A method of reconstructing a carpometacarpal (CMC) joint of a thumb of a hand, comprising:
   a) inserting an elongate tapered portion of an implant into a cavity formed in a metacarpal until an end face of an internal bulge of the implant circumferentially contacts a cortex of the metacarpal;
   b) positioning a scaphoid such that the scaphoid is in contact with a proximal face of an articulation bulge of the implant;
   c) stripping away a portion of a tendon to leave a distal attachment intact adjacent to the implant;
   d) wrapping the portion of the tendon around a tapered neck of the implant to a point intersecting a remaining tendon at a palm side of the hand in the absence of threading any portion of the tendon through an aperture, the tapered neck disposed between the internal bulge and the articulation bulge of the implant such that the tapered neck encircles the implant in a direction that is substantially perpendicular to a longitudinal axis of the elongate portion of the implant, wherein the portion of the tendon that is wrapped around the tapered neck at least partially encircles the longitudinal axis; and
   e) suturing the tendon to the remaining tendon.

8. The method of claim 7, wherein the tapered neck has a cross-sectional area that is less than a cross-sectional area of the internal bulge and a cross-sectional area of the articulation bulge.

9. The method of claim 7, wherein the elongate tapered portion includes an annular cross section and a substantially constant taper.

10. The method of claim 7, wherein the tapered neck includes a concave arcuate juncture formed between a proximal surface of the internal bulge and a distal surface of the articulation bulge.

11. The method of claim 10, wherein the concave arcuate juncture is symmetric about a longitudinal axis of said implant.

12. The method of claim 10, wherein the concave arcuate juncture flattens out to include a low-arched central region.

13. The method of claim 7, wherein step c) includes stripping away a portion of a flexor carpi radialis (FCR) tendon.

14. The method of claim 7, wherein step c) includes stripping away a portion of an abductor pollicis longus (APL) tendon.

* * * * *